United States Patent [19]
Silvis et al.

[11] Patent Number: 5,119,669
[45] Date of Patent: Jun. 9, 1992

[54] SLEEVE UNITS FOR INLET SPLITTERS OF CAPILLARY GAS CHROMATOGRAPHS

[75] Inventors: Paul H. Silvis, Lemont; Joseph W. Walsh, Bellefonte; David M. Shelow, State College, all of Pa.

[73] Assignee: Restek Corporation, Bellefonte, Pa.

[21] Appl. No.: 560,103

[22] Filed: Jul. 31, 1990

[51] Int. Cl.$^5$ .............................. G01N 30/38
[52] U.S. Cl. ........................ 73/23.41; 73/23.35
[58] Field of Search .............. 73/23.35, 23.39, 23.41, 73/19.02; 422/89; 436/161; 366/310, 339

[56] References Cited

U.S. PATENT DOCUMENTS

| | | |
|---|---|---|
| 3,327,520 | 6/1967 | Stapp, Jr. |
| 3,374,660 | 3/1968 | McKinney et al. |
| 3,401,565 | 9/1968 | Stoll et al. |
| 3,592,046 | 7/1971 | Cramers et al. |
| 3,672,226 | 6/1972 | Reid |
| 3,798,973 | 3/1974 | Estey ..................... 73/23.35 |
| 4,035,168 | 7/1977 | Jennings |
| 4,124,358 | 11/1978 | Muller |
| 4,187,856 | 2/1980 | Hall et al. |
| 4,242,227 | 12/1980 | Nestrick et al. |
| 4,405,344 | 9/1983 | Sisti et al. |
| 4,422,860 | 12/1983 | Feinstein |
| 4,474,588 | 10/1984 | Hinshaw, Jr. |
| 4,650,499 | 3/1987 | Scott |
| 4,704,141 | 11/1987 | Krebber |
| 4,835,058 | 5/1989 | Komiya et al. |
| 4,847,159 | 7/1989 | Glajch et al. |
| 4,878,925 | 11/1989 | Kojima ........................ 366/339 |

FOREIGN PATENT DOCUMENTS 1800838 4/1969 Fed. Rep. of Germany ..... 73/23.35

OTHER PUBLICATIONS

Grob, K. and Grob, G. "Splitless Injection on Capillary Columns, Part I. The Basic Technique"; Steroid Analysis as an Example: *Journal of Chromatographic Science*, vol. 7 (Oct. 1969) pp. 584–591.

Jones, R. A. *An Introduction To Gas-Liquid Chromatography*. Academic Press, London and New York, 1970. pp. 21–25.

Condon, R. D. "Design Considerations of a Gas Chromatography System Employing High Efficiency Golay Columns" *Analytical Chemistry*, vol. 31, No. 10 (Oct. 1959) pp. 1717–1722.

*Primary Examiner*—Hezron E. Williams
*Assistant Examiner*—Michael J. Brock

[57] ABSTRACT

A sleeve unit for converting a liquid sample into a sample gas and for mixing the sample gas and a carrier gas into a uniform gas mixture and delivering the gas mixture to the inlet end of a capillary tube of a gas chromatograph comprises a tubular liner having a bore, an inlet expansion chamber in the bore for changing a liquid sample into a sample gas, a mixing chamber in the bore next to the inlet chamber, a spiral core baffle inside the mixing chamber for thoroughly mixing the sample gas and the carrier gas into a uniform gas mixture by guiding the sample gas and the carrier gas into a spiral path around the spiral core baffle between the baffle and the liner, and an outlet chamber next to the mixing chamber for delivering the thoroughly mixed sample and carrier gases to an inlet end of a capillary tube of a gas chromatograph.

9 Claims, 2 Drawing Sheets

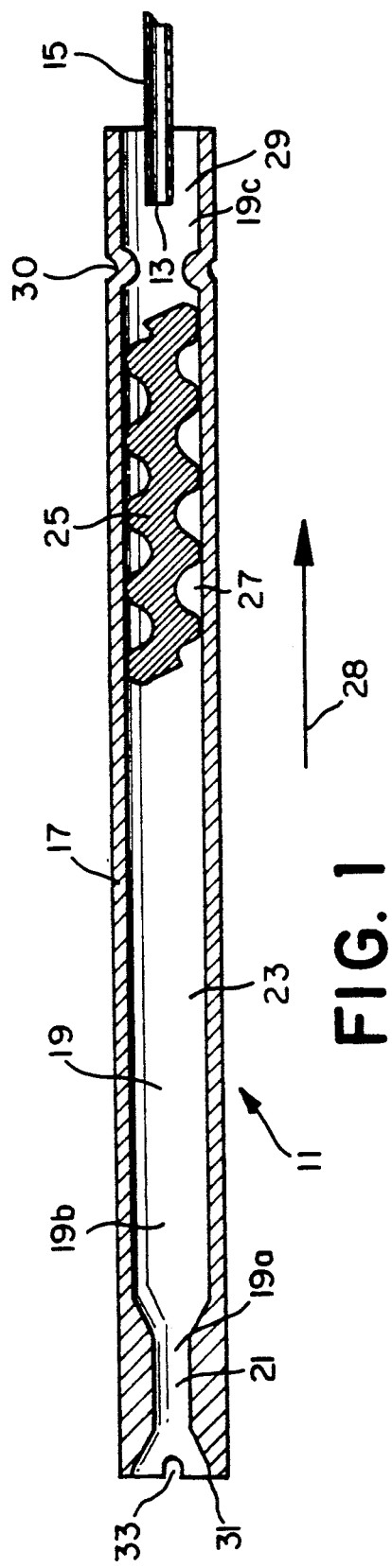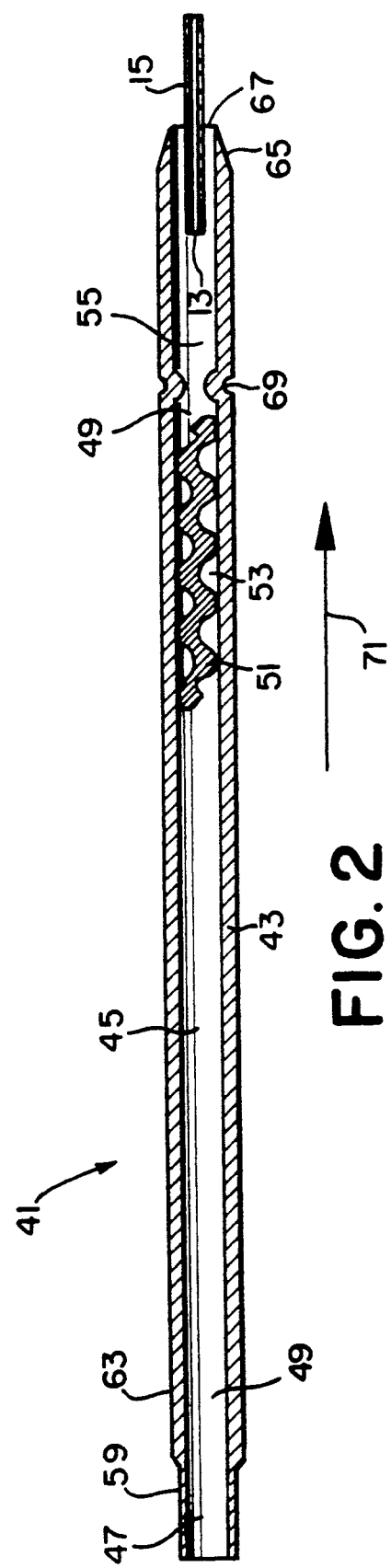

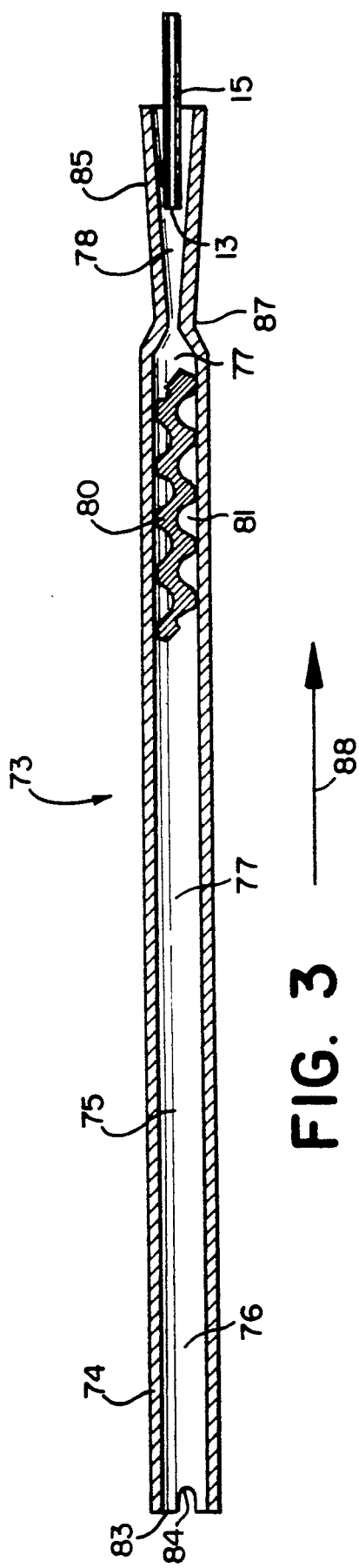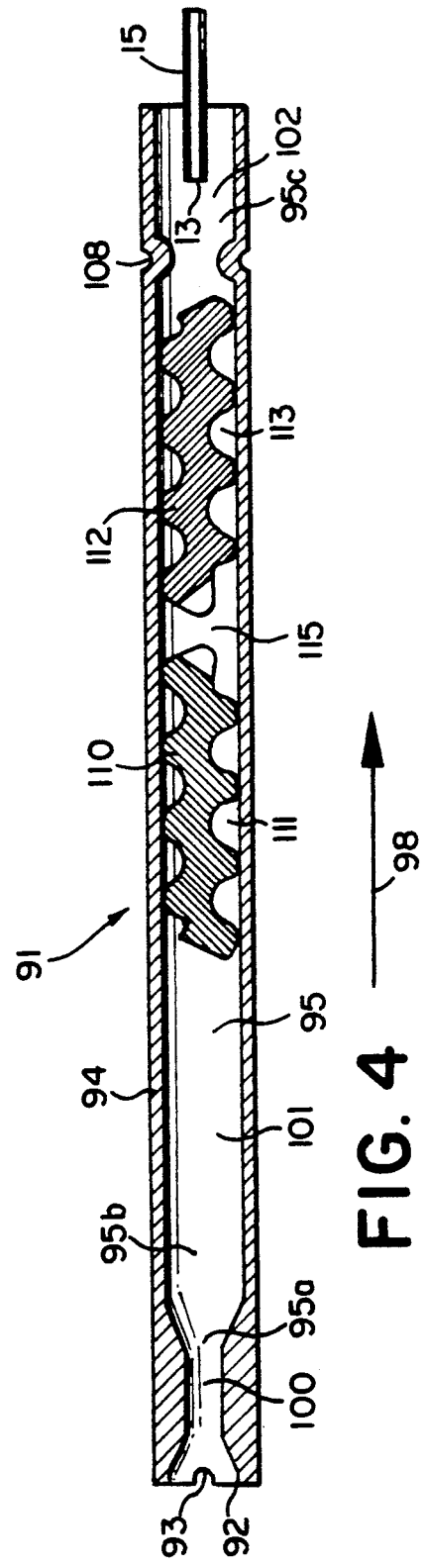

SLEEVE UNITS FOR INLET SPLITTERS OF CAPILLARY GAS CHROMATOGRAPHS

BACKGROUND OF THE INVENTION

1. Field of the Invention

This invention relates to inlets for capillary gas chromatographs, and more particularly concerns sleeve units for inlet splitters wherein a liquid sample is vaporized into a sample gas and mixed with a carrier gas, and a portion of the gas mixture is split off and delivered to the inlet end of a capillary tube of a gas chromatograph, for splitless sleeves where most of the sample gas reaches the capillary tube, for direct injection and for Septumless Programmable Injectors (SPI) or Programmable Temperature Vaporizing (PTV) Injectors.

2. Description of the Prior Art

Inlet splitters for gas chromatographs are shown and described in Jennings U.S. Pat. No. 4,035,168, issued Jul. 12, 1977, and in an article cited in that patent entitled "Design Considerations and Construction of a Superior Inlet Splitter," by A. J. Ehrler, Victoreen on Chromatography, Issue No. 4 (undated), Victoreen Instrument Division. Both of these documents are incorporated herein by reference, and a copy of each is enclosed.

In the Jennings patent, there is shown in FIGS. 1, 3 and 8 an inlet splitter 10 that is provided with a sleeve unit that comprises a tubular inner liner 66 with a central bore 68 having an inlet opening 72 and an outlet end 76, a rearwardly directed cup baffle 78, a forwardly directed cup baffle 82, a constriction 86 for further turbulent intermixing, and an expansion zone 88 with a terminal portion 90.

The Jennings patent also shows a sleeve unit in FIGS. 6 and 7 which comprises a tubular liner 66 having a bore 68, a rearwardly facing cup baffle 78, a forwardly directed cup baffle 82, dimples 118, and an expansion zone 88 with a terminal portion 90.

Jennings shows another sleeve unit in his FIG. 9 which comprises a tubular liner 166 having a bore 168, a flow restricting baffle 176 which is coupled with a rearwardly facing cup baffle 178, and an expansion zone 142 in which is positioned inlet end 180 of a capillary tube 156 associated with a chromatograph.

In Jennings, as in other splitter units for capillary gas chromatography, the liquid samples are generally introduced into the sleeve unit by a small volume syringe through a rubber septum, for example, Jennings' rubber septum 54.

A problem with the Jennings splitter 10 is that with repeated injections of liquid sample, the self-sealing cap or rubber septum 54 tends to fragment and pieces drop into the bore 68 of the tubular liner 66. While it is a simple matter to remove the sleeve unit and try to rinse out the fragments with some solvent, the Jennings cup design makes it very difficult to rinse clean the sleeve unit. Once fragments collect in the cup, it is virtually impossible to rinse them out.

The Jennings cup splitter sleeve unit has been a standard in the industry for many years. It has many of the features that are generally desired. It is made from glass which is less reactive than metal. The flow path that the carrier gas and sample go through is forced to change directions in the cup or invertor region. This rather abrupt change in direction creates turbulence inside the sleeve unit, and this turbulence is desirable because it promotes mixing of the sample gas with the carrier gas. When the mixed gases finally reach the capillary column, only a small portion of it enters the column and the rest of it exits through the split vent. In this way, the amount or volume gas that is introduced to the column is cut down. In other words, a portion of the mixed gas is split out from the main portion and is directed to the column. Hence, the name splitter sleeve unit.

It is very important that the sample be well mixed with the carrier gas before "splitting" so that a representative portion of the sample reaches the column. For example, if you want one percent (1%) of the sample mixture in the column, you may get one percent of one component and more or less of other components. This non-linearity is undesirable. The cup splitter sleeve unit seems to overcome this problem of non-linearity of the split sample. However, the cup splitter sleeve unit does have a drawback in that it is difficult to clean.

SUMMARY OF THE INVENTION

The sleeve unit of the present invention is made and sold by Restek Corporation, Bellefonte, Pa. 16823-8812, under the trademark CYCLOSPLITTER sleeve unit. It allows for good turbulent mixing of the sample and the carrier gas, and also allows for easy rinsing of particles or fragments from the sleeve unit because there is no real path obstruction, and this makes the CYCLOSPLITTER sleeve unit easier to clean.

The invention comprises a sleeve unit for inlet splitters of capillary gas chromatographs which permits the insertion of a liquid sample which is vaporized and mixed with a carrier gas and conducts the mixed gas to the inlet portion of a capillary tube in a gas chromatograph. The parts of the sleeve unit may include an inert tubular glass liner, which may be deactivated, having an axially aligned spiral glass core functioning as a baffle for mixing the sample gas and the carrier gas together. The sleeve unit provides an inert glass surface for the vaporization of the liquid sample and for the turbulent mixing of the sample gas and carrier gas, as well as providing a substantially unreactive pathway or surface, when deactivated, which avoids the problems associated with reversible and irreversible adsorption.

BRIEF DESCRIPTION OF THE DRAWINGS

FIG. 1 is a view in cross-section of a sleeve unit for inlet splitters of capillary gas chromatographs, constructed in accordance with this invention;

FIG. 2 is a view in cross-section of a second embodiment of the invention.

FIG. 3 is a view in cross-section of a third embodiment of the invention; and

FIG. 4 is a view in cross-section of a fourth embodiment of the invention.

DETAILED DESCRIPTION OF THE DRAWINGS

Turning now to the drawings, there is shown in FIG. 1 a view in cross-section of a sleeve unit 11 for mixing a sample and a carrier gas into a uniform gas mixture and delivering the gas mixture to inlet end 13 of a capillary tube 15 or column of a gas chromatograph for analysis. Sleeve unit 11 comprises a tubular liner 17 having a bore 19. An inlet expansion chamber 21 is formed in the bore 19 and, in operation, it is heated to change a liquid sample inserted into the inlet chamber 21 into a sample gas. A mixing chamber 23 is provided in the bore 19 next to the inlet chamber 21, and a spiral core baffle 25 is positioned inside the mixing chamber 23 for thoroughly mixing the sample gas and the carrier gas into a uniform gas mixture by guiding the sample gas and carrier gas into a spiral path 27 around the spiral core baffle 25 between the baffle 25 and the liner 17. The direction of gas flow through sleeve unit 11 is as indicated by the arrow 28.

An outlet chamber 29 is positioned next to mixing chamber 23 and may be separated therefrom by dimples 30. Outlet sample 29 delivers the thoroughly mixed sample and carrier gases to the inlet end 13 of the capillary tube 15 of the gas chromatograph.

The inlet chamber 21 has a top edge 31 with a notch 33 that insures that the carrier gas has access to the bore 19 of the sleeve unit 11.

The bore 19a of inlet expansion chamber 21 is smaller than the bore 19b of the mixing chamber 23 and bore 19c of the outlet chamber 29.

The spiral core baffle 25 may have 2 turns per inch of core length but preferably has about 8 turns per inch, and the turns may be clockwise or counter-clockwise.

The liner 17 and the core baffle 25 are preferably made of glass or fused silica, and the core baffle 25 is fixed in place inside the liner 17 by an adhesive or by applying heat to the edges of the spiral to melt the edges and attach them to the inner surface of liner 17.

Turning now to FIG. 2, there is shown another embodiment of the invention which comprises sleeve unit 41 for mixing sample and carrier gases into a uniform gas mixture and delivering the gas mixture to the inlet end 13 of capillary tube 15 of a gas chromatograph for analysis. Sleeve unit 41 comprises a tubular liner 43 having a bore 45 with an inlet expansion chamber 47 which is subjected to heat to change a liquid sample inserted into the chamber 47 into a sample gas.

A mixing chamber 49 is provided in the bore 45 next to the inlet chamber 47 for thoroughly mixing the gases. A spiral core baffle 51 is positioned inside the mixing chamber 49 for guiding the sample and carrier gases in a spiral path 53 around the spiral core baffle 51 between the baffle 51 and the liner 43.

An outlet chamber 55 is positioned next to the mixing chamber 49 for delivering the thoroughly mixed sample and carrier gases to inlet end 13 of capillary tube 15 of the gas chromatograph.

The exterior diameter 59 of inlet chamber 47 is smaller than the exterior diameter 63 of the mixing chamber 49.

The outlet chamber 55 is provided with a tapered or chamfered end portion 65 by grinding to fit into a graphite seal and to form an outlet opening 67 that accommodates the capillary tube 15.

The liner 43 and the core baffle 51 are preferably made of glass or of fused silica, and the baffle 51 is connected to the liner 43 by an adhesive or the edges of baffle 51 are melted and sealed against the line 43.

Dimples 69 may be provided in liner 43 between mixing chamber 49 and outlet chamber 55. The direction of gas flow through sleeve unit 11 is indicated by arrow 71.

Turning now to the embodiment of the invention illustrated in FIG. 3, there is shown a sleeve unit 73 for mixing sample and carrier gases into a uniform gas mixture and delivering the gas mixture to the inlet end 13 of capillary tube 15 of a gas chromatograph. Sleeve unit 73 comprises a tubular liner 74 having a bore 75 with an inlet expansion chamber 76 which is heated to exchange a liquid sample inserted into chamber 76 into a sample gas.

A mixing chamber 77 is provided in bore 75 next to inlet chamber 76 and the gases are thoroughly mixed in the mixing chamber 77. An outlet chamber 78 is provided next to the mixing chamber 77 for delivering the thoroughly mixed sample and carrier gases to inlet end 13 of capillary tube 15 of the gas chromatograph.

To assist in the thorough mixing of the sample and carrier gases, a spiral core baffle or screw 80 is positioned inside mixing chamber 77 for guiding the mixed gases in a spiral path 81 around the spiral core baffle 80. The spiral path 81 passes through the spiral opening formed between the baffle 80 and the interior surface of the liner 74.

Outlet chamber 78 has a radial taper 85 which forms a press fit seal around the capillary column 15. If capillary column 15 is pushed into taper portion 85 as far as it goes, a gas-tight seal is formed between sleeve portion 85 and the capillary column 15. The direction of flow through sleeve unit 73 is indicated by direction arrow 88.

At the upper end of sleeve unit 73, edge 83 of the sleeve unit 73 is provided with a notch 84 which allows carrier gas into the sleeve unit since top edge 83 is held against the rubber septum which seals the injection port.

The embodiment of sleeve unit 73 shown in FIG. 3 is a direct injection sleeve, and a restriction 87 separates the mixing chamber 77 from the outlet expansion chamber 78.

Turning now to the fourth embodiment of the invention which is shown in FIG. 4, a sleeve unit 91 has an upper edge 92 with a notch 93, a tubular liner 94 with a bore 95, an inlet expansion chamber 100, a mixing chamber 101, and an outlet chamber 102. A dimple 108 in liner 94 separates the mixing chamber 101 from the outlet chamber 102.

To assist in mixing the gases into a uniform gas mixture, a first spiral core baffle or screw 110 is positioned in the mixing chamber 101 and has its spiral in the clockwise direction to provide a clockwise spiral path 111 between the screw 110 and the interior surface of the tubular liner 94.

A second spiral baffle or screw 112 is positioned in mixing chamber 101 near the dimples 108 and has a counterclockwise spiral which provides a counterclockwise spiral path 113 between the second screw 112 and the interior surface of liner 94.

Between the screws 110 and 112 there is provided a reversal chamber 115 wherein the direction of the gas mixture is changed from clockwise to counterclockwise to assist in thoroughly mixing the gases.

Inlet expansion chamber 100 is provided with an inlet bore 95a, mixing chamber 101 is provided with a mixing bore 95b, and outlet chamber 102 is provided with an outlet bore 95c, and the direction of gas flow is indicated by the direction arrow 98.

The method of the invention for mixing a fluid sample and a carrier gas into a uniform gas mixture and delivering the gas mixture to the inlet end 13 of a capillary tube 15 of a gas chromatograph for analysis, comprises the steps of, referring to FIG. 1 for example, providing a sleeve unit 11 having a tubular liner 17 which has a bore 19, an inlet expansion chamber 21 in the bore 19 for changing the liquid sample into a gas sample when subjected to heat, a mixing chamber 23 in the bore 19 next to the inlet chamber 21, a spiral core 25 baffle inside the mixing chamber 23 for thoroughly mixing the sample gas and the carrier gas into a uniform gas mixture by guiding the sample gas and carrier gas into a spiral path 27 around the spiral core baffle 25 between the baffle 25 and the interior surface of the liner 17, and an outlet chamber 29 next to the mixing chamber 23 for delivering the thoroughly mixed gases to an inlet end 13 of a capillary tube 15 of a gas chromatograph; inserting a liquid sample into the inlet expansion chamber 21; heating the liquid sample to convert it into a gas sample in the expansion chamber 21; inserting a carrier gas into the expansion chamber 21; moving the sample gas and carrier gas into the mixing chamber 23; moving the sample gas and carrier gas in a spiral path 27 around the spiral core baffle 25 between the baffle 25 and the interior surface of the liner 17 to thoroughly mix the gases together into a uniform gas mixture; and delivering the gas mixture to the outlet chamber 29 and to the inlet end 13 of a capillary tube or column 15 of a gas chromatograph.

The glass screw or spiral baffle which is incorporated into the inventive sleeve units provides benefits for split, splitless, and direct injection methods of handling liquid samples. The sleeve units of the present invention provide for less splitter discrimination, and do a better job of trapping non-volatile residue than glass wool, glass beads, packings, or ceramic frits. Such residue travels approximately one turn around the glass screw which minimizes interaction with sensitive, highly active sample components which are prone to decomposition and adsorption. Chromatographs analyzing everything from pesticides to dirty environmental samples may take a larger number of injected samples before non-volatile residue affects calibration linearity when using the sleeve units of the present invention as compared to splitter units using glass wool, glass beads, or any other inlet packing. Accordingly, productivity goes up because maintenance is required less often. In addition, the glass screw is much more inert than wool, beads, packings and ceramic frits. The sleeve units have been successfully used in direct injection devices for 0.32 and 0.53 mm internal diameter capillary columns as well as in split and splitless units.

Certain inside diameters of chromatograph columns necessitate the introduction of only a small amount of sample material on the order of 0.01 microliter in order to avoid the problems associated with overloading the system, and the sleeve units of the present invention are designed to aid in meeting that requirement when used with a split injection system.

The inlet splitter sleeve unit of the present invention provides an inert pathway along with a vaporization and mixing region followed by a zone that allows the vaporized sample gas mixture to pass over the head of the capillary tube so that only a small portion or aliquot is actually transferred to the interior of the capillary tube and the remainder passes out of the apparatus through a vent.

Sleeve units of the present invention have been deactivated with organochlorosilanes, organodichlorosilanes, organoalkoxysilanes, hydrosilanes, polyoxyethylenes, organodisilazanes, or other deactivating compositions.

The placing of glass wool inside sleeve units has the benefit of providing a greater surface area of the fibers. However, the fibers are fragile and may break and adsorb compounds and produce incorrect test results. The spiral core baffles of the present invention avoid these problems.

We claim:

1. A sleeve unit for converting a liquid sample into a sample gas and for mixing the sample gas and a carrier gas into a uniform gas mixture and delivering the gas mixture to the inlet end of a capillary tube of a gas chromatograph for analysis, comprising
    a tubular linear having a bore with an inside surface,
    an inlet expansion chamber in the bore for changing a liquid sample into a sample gas,
    a mixing chamber in the bore next to the inlet chamber for thoroughly mixing the sample and carrier gases together,
    a spiral core baffle inside the mixing chamber means for thoroughly mixing the sample gas and the carrier gas into a uniform gas mixture by guiding the sample gas and carrier gas into a spiral path around the spiral core baffle between the baffle and the liner bore,
    an outlet chamber next to the mixing chamber for delivering the thoroughly mixed sample and carrier gases to an inlet end of a capillary tube of a gas chromatograph,
    said spiral core baffle having spiral edges,
    and means affixing the edges of the spiral core to the inside surface of the bore of the bore to hold the spiral core in fixed position relative to the tubular liner.

2. The sleeve unit of claim 1,
    said inlet expansion chamber having a top edge with a notch to insure that the carrier gas has access to the bore of the sleeve unit.

3. The sleeve unit of claim 1,
    the interior and exterior diameters of the liner being smaller at the inlet chamber than at the mixing chamber.

4. The sleeve unit of claim 1, including
    said outlet chamber having a tapered end portion.

5. The sleeve unit of claim 1,
    said spiral core baffle having about eight turns per inch of core length.

6. The sleeve unit of claim 1,
    said spiral core baffle being two spiral cores with one having a clockwise spiral and the other having a counterclockwise spiral to reverse the rotation of gas flow and assist in mixing the gases.

7. A method of mixing a sample gas and a carrier gas into a uniform gas mixture and delivering the gas mixture to the inlet end of a capillary tube of a gas chromatograph for analysis, comprising the steps of
    providing a tubular liner having a bore, an inlet expansion chamber in the bore for changing a liquid sample to a sample gas, a mixing chamber in the bore next to the inlet chamber, a spiral core baffle in fixed position inside the mixing chamber for thoroughly mixing the sample gas and the carrier gas into a uniform gas mixture by guiding the sample gas and carrier gas into a fixed spiral path around the fixed spiral core baffle between the baffle and the liner, and an outlet chamber next to the mixing chamber for delivering the thoroughly mixed sample and carrier gases to an inlet end of a capillary tube of a gas chromatograph,
    inserting a liquid sample into the inlet expansion chamber,
    heating the liquid sample in the expansion chamber to expand it into a gas sample, inserting a carrier gas into the inlet expansion chamber, moving the sample gas and the carrier gas into the mixing chamber, moving the sample gas and carrier gas in a fixed spiral path around the fixed spiral core baffle between the baffle core and the liner to thoroughly mix the gases together into a uniform gas mixture, delivering the gas mixture to the outlet chamber, and delivering a portion of the gas mixture to the inlet end of a capillary tube of a gas chromatograph.

8. The method of claim 7, including moving the sample gas and carrier gas in a fixed spiral path around the fixed spiral core baffle between the baffle core and the liner to thoroughly mix the gases together into a uniform gas mixture in a clockwise direction, and then moving the sample gas and the carrier gas in a fixed spiral path around the fixed spiral core baffle between the baffle core and the liner to thoroughly mix the gases together into a uniform gas mixture in a counter-clockwise direction.

9. The method of claim 7, including moving the sample gas and carrier gas in a fixed spiral path around the fixed spiral core baffle between the baffle core and the liner to thoroughly mix the gases together into a uniform gas mixture in a counter-clockwise direction, and then moving the sample gas and the carrier gas in a fixed spiral path around the fixed spiral core baffle between the baffle core and the liner to thoroughly mix the gases together into a uniform gas mixture in a clockwise direction.

* * * * *